United States Patent [19]

Imaki et al.

[11] 4,177,126

[45] Dec. 4, 1979

[54] REFERENCE ELECTRODE

[75] Inventors: Masakatu Imaki; Hidehiko Hagiwara; Seiji Usui, all of Kyoto, Japan

[73] Assignee: Horiba, Ltd., Japan

[21] Appl. No.: 917,352

[22] Filed: Jun. 20, 1978

[30] Foreign Application Priority Data

Jun. 20, 1977 [JP] Japan .............................. 52/80962[U]

[51] Int. Cl.² ...................... G01N 27/28; G01N 27/40
[52] U.S. Cl. ................................................. 204/195 F
[58] Field of Search ..................................... 204/195 F

[56] References Cited

U.S. PATENT DOCUMENTS

| | | | |
|---|---|---|---|
| 3,498,899 | 3/1970 | Kater et al. | 204/195 F |
| 3,505,196 | 4/1970 | Dahms | 204/195 F |
| 3,686,091 | 8/1972 | Sawa et al. | 204/195 F |
| 4,002,547 | 1/1977 | Neti et al. | 204/195 F |
| 4,053,382 | 10/1977 | Maruyama et al. | 204/195 F |

*Primary Examiner*—T. Tung
*Attorney, Agent, or Firm*—Wenderoth, Lind & Ponack

[57] ABSTRACT

A reference electrode includes a holder member having therein a chamber. An inner electrode is positioned within the chamber, the inner electrode being connected to an electric lead extending through an upper end of the holder member. The holder member has a lower end which is closed by a liquid junction in the form of a hydrophilic polypropylene membrane coated with a surface active agent. The membrane has an integral flange which fits around the lower end of the holder member, and the membrane is readily selectively removable from the lower end of the holder member.

3 Claims, 4 Drawing Figures

REFERENCE ELECTRODE

BACKGROUND OF THE INVENTION

The present invention relates to a reference electrode of the type used in testing or measuring various samples, such as serum or a blood sample.

More particularly, the present invention relates to such a reference electrode of the type including an internal electrode provided within a chamber within a cylindrical holder, the chamber being filled with a reference fluid which is connected to the exterior of the reference electrode by means of a liquid junction at the lower end thereof.

Reference electrodes of the above general type are known and have generally employed liquid junctions of the so-called sleeve type, pinhole type or ceramic type. All of these prior art types of liquid junctions however have suffered from certain inherent disadvantages.

Liquid junctions of the sleeve type are normally formed of an inner tube portion having therein a penetrating hole and an outer tube portion or sleeve which is attached to the outer peripheral surface of the inner tube by mutual friction. This type of liquid junction is disadvantageous in that a considerable amount of inner fluid or liquor leaks therefrom, and in that it is virtually impossible to manufacture this type of liquid junction of a very small size, whereby the device cannot be employed for the measurement of a small amount of a sample.

Liquid junctions of the pinhole type include a member having a small hole therein. This type of liquid junction however, is disadvantageous in that such pinhole is readily susceptible to being filled up with foreign solid substances from the exterior. Thus, this type of liquid junction cannot be employed for the measurement of a sample solution containing organic or other foreign substances having a tendency to deposit.

Furthermore, liquid junctions formed of a ceramic material are also very easily filled up with foreign solid matter such as organic polymeric substances, particularly protein substances when the electrode is used for the measurement of blood or serum. Also, liquid junctions of the ceramic type allow a considerable leakage of the inner liquor, thereby making it necessary to frequently supplement the supply of liquor to the inner chamber of the reference electrode. Thus, a reference electrode including a liquid junction of the ceramic type normally includes a rubber stopper which must be removed to replenish the supply of inner liquor. This type of operation however may easily result in spilling of the inner liquor. For the above reasons, reference electrodes employing liquid junctions of the ceramic type are quite disadvantageous from the standpoint of handling and are also uneconomical.

SUMMARY OF THE INVENTION

With the above discussion in mind, it is a primary object of the present invention to provide an improved reference electrode which overcomes the above discussed disadvantages of the prior art.

It is a further object of the present invention to provide such an improved reference electrode which has great flexibility in size and which is less expensive to manufacture and maintain than prior art reference electrodes.

The above objects are achieved in accordance with the present invention by the provision of a reference electrode including a holder member having therein a chamber, an inner electrode positioned within the chamber, the inner electrode being connected to an electric lead extending through an upper end of the holder member, and the holder member having a lower end closed by a liquid junction formed of a hydrophilic polypropylene membrane coated with a surface active agent. The membrane is fitted on the lower end of the holder member so as to be readily selectively removable therefrom. By the use of such a liquid junction, the liquid junction will not be filled up with foreign substances. Even further, the liquid junction in accordance with the present invention provides a much more stable electrode potential than is achievable with prior art devices. Further, the electrode of the present invention is less expensive to maintain than prior art electrodes, in that the entire reference electrode may be refurbished by merely replacing the liquid junction portion itself, which forms only the lowermost end portion of the reference electrode.

BRIEF DESCRIPTION OF THE DRAWINGS

Other objects, features and advantages of the present invention will become apparent from the following detailed description, taken with the accompanying drawings, wherein.

DETAILED DESCRIPTION OF THE INVENTION

Figure 1:
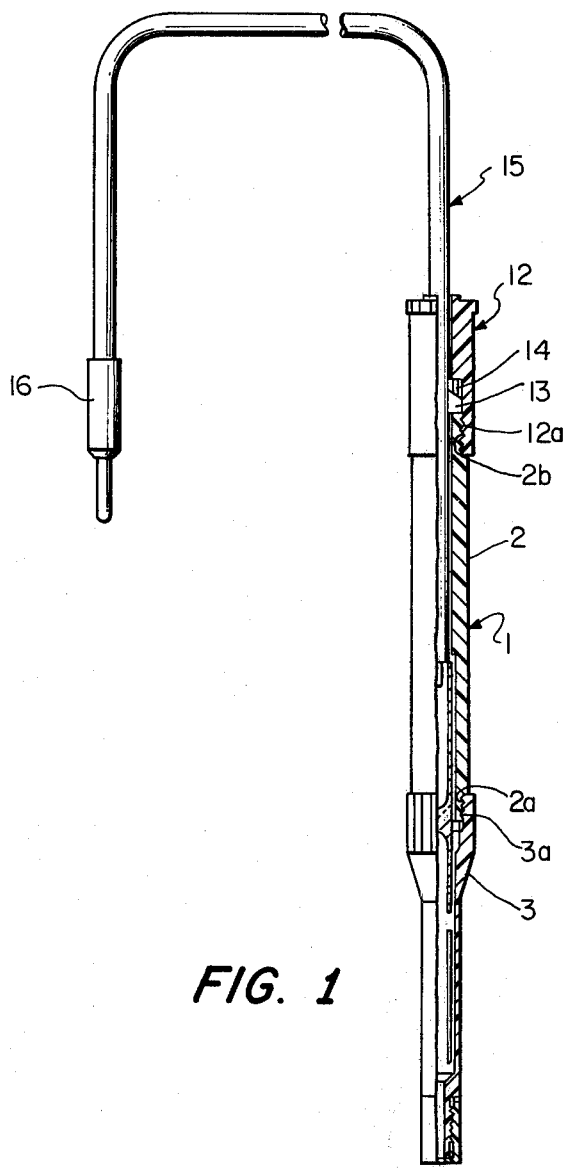
FIG. 1 is an elevation view, with portions broken away, of one embodiment of a reference electrode in accordance with the present invention.

With reference now to FIG. 1 of the drawings, the overall structure of the reference electrode of the present invention will be described. In this regard, certain conventional aspects of the reference electrode and the manner of use and application thereof are well known in the art and thus are not described herein.

The reference electrode, generally designated by reference numeral 1, is preferably of a cylindrical or tubular configuration, although other configurations are possible, and includes an upper holder 2 and a lower holder 3. Holders 2 and 3 are formed of a suitable material, such as a synthetic resin material, for example polypropylene. The lower end of upper holder 2 and the upper end of lower holder 3 are joined to each other by suitable means, for example mating male screw threads 2a and female screw threads 3a, as shown in more detail in FIG. 2.

Figure 2:
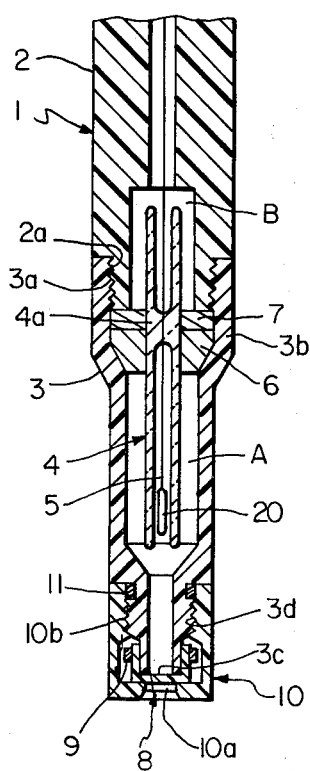
FIG. 2 is an enlarged cross-sectional view of the lower portion of the reference electrode shown in FIG. 1.

With specific reference now to FIG. 2 of the drawings, an inner electrode tube 4, prepared from a suitable glass material, is positioned within the interior of the cylindrical holder. Specifically, in the illustrated embodiment, the upper portion 3b of lower holder 3 has an enlarged diameter which forms an inclined seat which supports a bushing 6 formed of a suitable rubber material, such as silicone rubber, and a ring 7 formed of a suitable synthetic resin material, for example polypropylene. Inner electrode tube 4 extends through openings in bushing 6 and ring 7 and is thus firmly and sealingly positioned thereby in the interior of the cylindrical holder. As will be apparent from FIG. 2, the lower end of upper holder 2 is pressed against ring 7 by the tightening of mating threads 2a and 3a, whereby bushing 6 is caused to tightly contact the interior of lower holder 3 and the exterior of inner electrode tube 4. It will further be apparent from FIG. 2 that the interior of the cylindrical holder is divided into completely separated chambers A and B by means of bushing 6 and inner electrode tube 4.

An inner electrode 20 is positioned within the lower end of inner electrode tube 4 and is connected by lead wire 5 to a terminal 16, via a conduit 15. It is to be understood that the construction of conduit 15 and terminal 16 are conventional and are connectable in a known manner to other conventional testing equipment. Lead wire 5 may be formed of silver, but with a portion thereof embedded in a glass wall portion 4a of inner electrode tube 4 being formed of platinum.

The lower end of lower holder 3 has an opening 3c therein. This opening is covered by a hydrophilic plastic membrane 8 in accordance with the present invention. Preferably, membrane 8 has a tubular flange which fits around the lower end of lower holder 3 and is held tightly thereagainst by means of a push ring 9. As will be understood, chamber A is filled with a suitable reference solution, for example a conventional salt solution, during use of the reference electrode. Hydrophilic plastic membrane 8 operates in a known manner to allow diffusion therethrough of the fluid filling chamber A to provide a liquid junction with the exterior liquid being tested or measured.

Membrane 8 may be formed of any suitable plastic material which is hydrophilic, or which is rendered hydrophilic, which is compatible with the liquids in contact therewith, and which provides the desired porosity or permeability for the particular use involved.

Specific examples of materials which may be employed for the hydrophilic plastic membrane 8 are Duraguard 3401 or Duraguard 3501 manufactured by Polyplastic Corporation. Duraguard 3401 has a maximum porosity or opening dimension of 0.2 by 0.02 $\mu$m, a porosity of 38%, and a thickness of 25 $\mu$m. The corresponding specifications of Duraguard 3501 are 0.4 by 0.04 $\mu$m, 45% porosity, and 25 $\mu$m, respectively. Duraguard 3401 and 3501 membranes are prepared from polypropylene film which is coated with a surface active agent, and the rates of water permeability are 0.05 ml/cm$^2$.min and 0.5 ml/cm$^2$.min under a static pressure of 1 kg/cm$^2$, respectively.

Thus, the hydrophilic plastic membrane 8 of the present invention is preferably a polypropylene film coated by a surface active agent. It will be understood by those skilled in the art that the surface active agent employed may be any surface active agent which makes the film hydrophilic and which is compatible with the liquids employed in the reference electrode. Specifically, the surface active agents employed may be those employed by Polyplastic Corporation in the preparation of Duraguard 3401 and 3501.

It is to be further understood that the specific polypropylene film employed, and particularly the characteristics thereof such as porosity, thickness, and maximum opening dimension, may be varied as desired and as required by the specific use to which the reference electrode is applied.

With further reference to FIG. 2, a cap 10 is suitably attached to the lower end of lower holder 3, for example by mating threads 10b and 3d. A packing 11 ensures a fluid tight connection between lower holder 3 and cap 10. Cap 10 has therein a hold or opening 10a at a position corresponding to the location of the liquid junction formed by that portion of hydrophilic plastic membrane 8 which spans the opening 3c in lower holder 3.

With reference again to FIG. 1, the upper end of upper holder 2 is fitted with and closed by a cap 12 which is suitably attached to the upper end of holder 2, for example by engaging threads 2b and 12a. Conduit 15 extends through cap 12 and is fixedly and sealingly positioned therein by means of a bushing 13, for example of synthetic resin, and a resin 14. It will be apparent that the tightening of cap 12 onto holder 2 will cause bushing 13 to press against and fixedly position conduit 15.

In the event that it becomes necessary to exchange the membrane 8 or replace the fluid (not shown) within chamber A, then the electrode is merely inverted from the position shown in FIGS. 1 and 2, cap 10 is removed, then push ring 9 is pulled off, and membrane 8 may be simply removed from the free end of holder 3. To remove the fluid within chamber A, the needle of a syringe of suitable capacity may be introduced into chamber A, and the fluid therein may be thus withdrawn. Then, after suitably washing and cleansing the interior of the syringe, a fresh supply of fluid may be injected from the syringe into the chamber A, thus filling the chamber. Thereafter, a new membrane 8 may be placed over the free end of holder 3, and the push ring 9 is then applied over the flange of the new membrane, thus sealing and holding the membrane in position. Thereafter, the cap 10 is replaced.

Figure 3A:
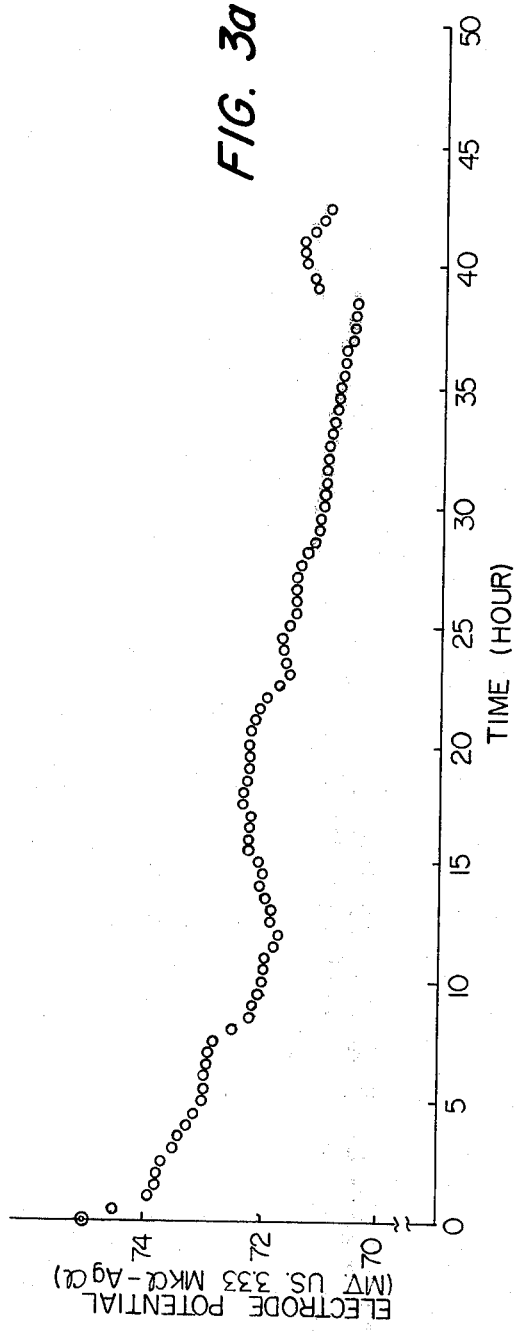
FIG. 3a is a graph illustrating the drift of electrical potential obtained by employing the reference electrode of the present invention.
Figure 3B:
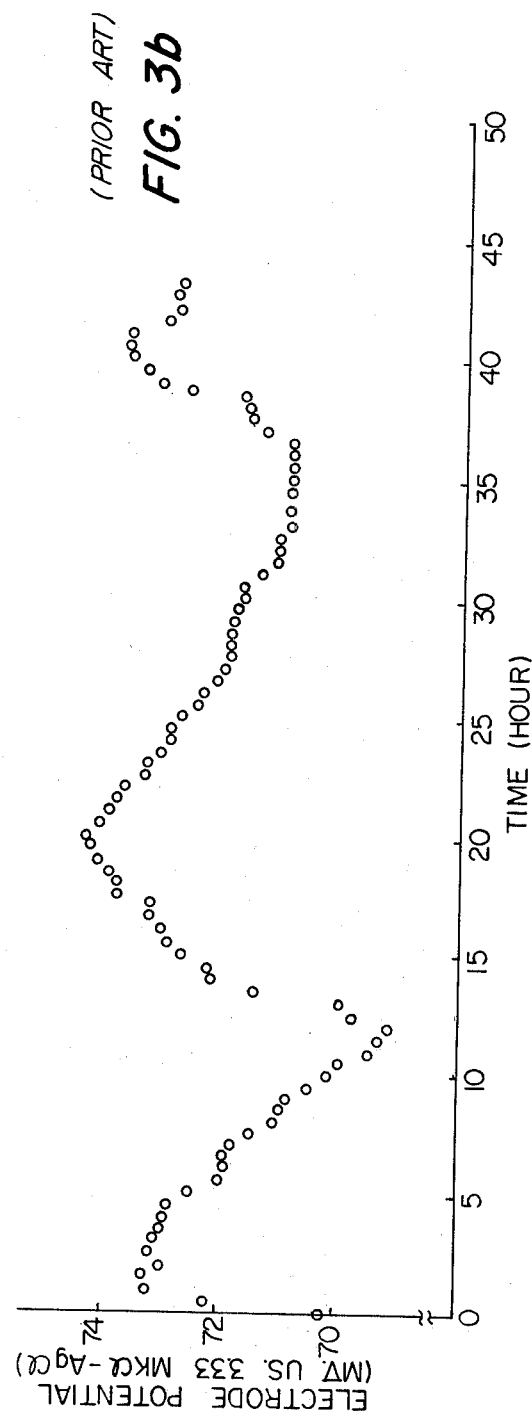
FIG. 3b is a graph similar to FIG. 3a, but illustrating the drift of electrical potential employing a conventional reference electrode of the ceramic type.

FIGS. 3a and 3b illustrated the improved performance of the reference electrode of the present invention (FIG. 3a) as compared with a conventional reference electrode having a liquid junction of the ceramic type (FIG. 3b). Specifically, the reference electrode in accordance with the present invention, the performance of which is illustrated in FIG. 3a, was formed of Duraguard 3401 as discussed above. As will be apparent from FIGS. 3a and 3b, the drift or fluctuation of the electrode potential of the respective reference electrodes, as a function of time, is much less with the reference electrode of the present invention than with the conventional reference electrode. That is, by using the reference electrode of the present invention, it is possible to ensure a much more stable electrode potential than is possible when employing the conventional reference electrode.

Furthermore, leakage of the inner fluid is much less in accordance with the reference electrode of the present invention than with the reference electrode of the prior art, since the inner liquid is forced to permeate through the membrane 8 only by the pressure originating from the weight of the liquid, and since the exterior of the membrane is always maintained in a wetted condition by contact thereof with the aqueous medium. In fact, it has been established that the decrease in the amount of the inner liquid is very small, even after a length of time of one month. The inner liquid employed to establish this fact was a solution of a serum diluted ten times (supporter electrolyte plus buffer), and the test was carried out using the solution in an amount of 200 ml at a temperature of 25.0±0.1° C.

In the event that it is important to reduce even further the amount of leakage of the inner liquid through the membrane, then the membrane 8 may be formed of Duraguard 2402 coated with a surface active agent. Duraguard 2402 is prepared by positioning a sheet of Duraguard 3401 between two sheets of Duraguard 2400 which are not coated with a surface active agent (all Duraguard films referred to herein being manufactured by Polyplastic Corporation).

As discussed above, the most critical feature of the present invention is the use of a polypropylene film coated with a surface active agent as the liquid junction of a reference electrode. This makes it possible for the reference electrode to have a stable standard electrode potential without the damger of the fine pores of the membrane filling with foreign precipitates such as organic high polymers, for example proteins which exist in serum or blood which may be tested.

Furthermore, even if it becomes necessary to replace the liquid junction portion of the reference electrode, in accordance with the present invention it is necessary to exchange only the membrane 8. This is an extreme advantage when compared with conventional prior art electrodes wherein it is necessary to exchange an entire holder or an entire electrode.

Even further, in accordance with the reference electrode of the present invention, and since the amount of leakage of the inner liquid from chamber A is extremely small, it is not necessary to continuously replenish the supply of internal liquid. This is particularly true when compared with the performance of conventional reference electrodes employing a liquid junction of the ceramic type.

Additionally, the structure of the liquid junction portion of the present invention is extremely simple to replace, since the membrane 8 can be easily removed and replaced by simply removing cap 10 and ring 9.

Yet further, since the liquid junction portion of the reference electrode of the present invention includes only the portion of membrane 8 covering the opening in the lower end of the cylindrical holder, the diameter of the holder can be made as small as necessary. This makes it possible to perform a measurement or a test on a sample of very small size.

In view of the above, it will be apparent that the reference electrode of the present invention is less expensive to manufacture, easier and less expensive to maintain, and provides more diversified applicability to the testing and measuring of serums, blood samples and other physical fluid substances, than is possible with prior art reference electrodes.

Although the present invention has been described above in detail with regard to a preferred embodiment thereof, it will be apparent to those skilled in the art that various modifications may be made to the specifically described and illustrated structural features, without departing from the scope of the present invention.

What we claim is:

1. A reference electrode for use in testing or measuring serum or blood samples, said reference electrode comprising:
    a cylindrical holder member including a cylindrical upper holder having upper and lower ends and a cylindrical lower holder having upper and lower ends, said lower end of said upper holder and said upper end of said lower holder being joined by meshing screw threads;
    said lower holder having an interior forming a chamber for containing a reference liquid;
    an inner electrode positioned within said chamber, said inner electrode being connected to an electric lead extending through said upper end of said upper holder;
    means for sporting said inner electrode within said chamber and for sealing said chamber adjacent said upper end of said lower holder;
    a liquid junction comprising a hydrophilic polypropylene membrane coated with a surface active agent, said membrane including a flat portion abutted against and closing said lower end of said lower holder and a tubular flange portion integral with and extending from said flat portion, said tubular flange portion fitting about an exterior surface adjacent said lower end of said lower holder; and
    a removable push ring surrounding said tubular flange portion and pressing said tubular flange portion tightly against said exterior surface.

2. A reference electrode as claimed in claim 1, further comprising a cap removably attached to an exterior portion of said lower holder adjacent said lower end thereof, said cap having therein an opening confronting that portion of said flat portion of said membrane which forms said liquid junction.

3. A reference electrode as claimed in claim 1, wherein said lower holder has formed therein adjacent said upper end thereof, an inner seat, and said supporting and sealing means comprises a resilient bushing supported on said seat, a ring mounted on said bushing, and an electrode tube extending through said bushing and said ring, said electrode being positioned within said electrode tube, said electrode tube having embedded therein a portion of said electric lead, and said lower end of said upper holder pressing said ring against said bushing, such that said bushing presses against said seat and said electrode tube.

* * * * *